United States Patent [19]

Naoi et al.

[11] Patent Number: 4,963,260
[45] Date of Patent: Oct. 16, 1990

[54] LIQUID FILTERING DEVICE

[75] Inventors: Keiji Naoi; Katsuhiko Iwata; Osamu Kaneko, all of Fuji, Japan

[73] Assignee: Terumo Kabushiki Kaisha, Tokyo, Japan

[21] Appl. No.: 321,650

[22] Filed: Mar. 10, 1989

[30] Foreign Application Priority Data

Mar. 15, 1988 [JP] Japan .................................. 63-60912

[51] Int. Cl.⁵ ............................................ B01D 29/56
[52] U.S. Cl. ................................... 210/446; 210/435; 210/456; 210/491; 210/492
[58] Field of Search ................ 210/435, 437, 441, 446, 210/447, 456, 491, 492, 445, 489, 490; 604/406

[56] References Cited

U.S. PATENT DOCUMENTS 4,009,714  3/1977  Hammer .............................. 210/445
4,422,939 12/1983  Sharp et al. ......................... 210/447
4,701,267 10/1987  Watanabe et al. ................... 210/491

FOREIGN PATENT DOCUMENTS 57-25222  5/1982  Japan .

Primary Examiner—W. Gary Jones
Attorney, Agent, or Firm—Frishauf, Holtz, Goodman & Woodward

[57] ABSTRACT

A liquid filtering device for separating leukocytes from blood to produce concentrated red cells, for example, includes a housing having a liquid inlet port and a liquid outlet port and providing a flow passage from the liquid inlet port to the liquid outlet port, a partition plate fixedly disposed in the housing, a first filter element disposed in the housing in an upstream position with respect to the flow passage, and a second filter element disposed in the housing in a downstream position with respect to the flow passage, the second filter element being made of a material having a larger filtration resistance than the first filter element. The second filter element has an outer peripheral edge fixed directly to the partition plate in a liquidtight manner in surrounding relation to the first filter element.

8 Claims, 8 Drawing Sheets

LIQUID FILTERING DEVICE

BACKGROUND OF THE INVENTION

The present invention relates to a liquid filtering device, and more particularly to a liquid filtering device for filtering out leukocytes and other components from blood and extracting red cells only to produce concentrated red cells.

Filtering devices are employed to filter a liquid to obtain a necessary component from the liquid. In order to achieve satisfactory separation performance and stabilize liquid processing capability, it is desired that any clogging of the filter element of the filtering device be minimized. To effect component transfusion on a patient who needs only red cells, for example, it is customary to obtain concentrated red cells through a centrifugal separation process, and the produced concentrated red cells are administered to the patient. Since the solution containing concentrated red cells also contains many leukocytes and platelets, it is not preferable to transfuse this solution to the patient who needs only red cells.

There has been employed a filtering process for increasing the purity of concentrated red cells (a red cell preparation) by removing leukocytes and platelets. The filtering process uses a main filter element for filtering out leukocytes and platelets and a preliminary filter element which has a smaller apparent density and a lower filtration resistance than the main filter element in order to reduce clogging in the main filter element.

One conventional liquid filtering device for producing highly pure red cell preparations is shown in FIG. 1 of the accompanying drawings. The liquid filtering device has a housing 2 in the form of a flat plate which defines a space 4 therein that is centrally divided by a partition plate 6 disposed in the housing 2. The partition plate 6 has a liquid inlet port 8 defined in an upper end thereof, and a liquid outlet port 10 defined in a lower end thereof. First filter elements 12a, 12b be applied to the partition plate 6 in sandwiching relation thereto, and second filter elements 14a, 14b are placed over the first filter elements 12a, 12b, respectively. The second filter elements 14a, 14b are pressed against the first filter elements 12a, 12b, respectively, by a plurality of projections 16 on inner wall surfaces of the housing 2.

The first filter elements 12a, 12b serve as preliminary filter elements for minimizing clogging in the second filter elements 14a, 14b. Therefore, the first filter elements 12a, 12b are coarser than the second filter elements 14a, 14b, and are made of nonwoven fabric of polyester, nylon, or the like which has a smaller apparent density than the second filter elements 14a, 14b.

The second filter elements 14a, 14b have a larger filtration resistance than the first filter elements 12a, 12b. Preferably, the second filter elements 14a, 14b are made of a porous material such as of synthetic resin or a nonwoven fabric of ultrathin fibers. In the conventional filtering device shown in FIG. 1, however, the first filter elements 12a, 12b and the second filter elements 14a, 14b are merely pressed against each other in superposed relation and fixedly positioned in the housing 2. During a filtering process, a liquid to be filtered, typically blood, may flow between the pressed regions of the first filter elements 12a, 12b and the second filter elements 14a, 14b, a phenomenon known as "short pass", and may directly go unfiltered into the liquid outlet port 10. Thus, the liquid is not effectively filtered by the second filter elements 14a, 14b. As a result, the ratio or percentage of removed leukocytes, i.e., the leukocyte removal ratio, is lowered. When the filtration resistance of the second filter elements 14a, 14b is increased by clogging, the first filter elements 12a, 12b are liable to be separated from the partition 6, and the liquid which is not filtered at all may be directed toward the liquid outlet port 10. Consequently, the conventional liquid filtering device has proven unsatisfactory.

SUMMARY OF THE INVENTION

It is an object of the present invention to provide a liquid filtering device which is capable of preventing a short pass of a liquid to be filtered and also preventing filter elements from being separated.

Another object of the present invention is to provide a liquid filtering device which has filter elements that can maintain a sufficient removal ratio and reduce clogging therein.

Still another object of the present invention is to provide a liquid filtering device including a first filter element which is relatively coarse and a second filter element which has a relatively large filtration resistance and is disposed in surrounding relation to the first filter element, the second filter element being mounted on a partition plate in a liquidtight manner to prevent the first and second filter elements from being separated from each other and also prevent the first filter element from being peeled off the partition plate.

Yet another object of the present invention is to provide a liquid filtering device which is simple in structure, can be manufactured inexpensively, and has a sufficient liquid filtering capability.

A further object of the present invention is to provide a liquid filtering device comprising: a housing having a liquid inlet port and a liquid outlet port; a partition plate fixedly disposed in said housing; a first filter element disposed in said housing in an upstream position with respect to a direction in which a liquid to be filtered flows from said liquid inlet port to said liquid outlet port; and second filter element disposed in said housing in a downstream position with respect to said direction, said second filter element being made of a material having a larger filtration resistance than said first filter element, said second filter element having an outer peripheral edge fixed directly to said partition plate in a liquidtight manner in surrounding relation to said first filter element.

A still further object of the present invention is to provide a liquid filtering device wherein said housing comprises a frame and a pair of lids fitted in opposite sides of said frame and closing the frame in a liquidtight manner, said partition plate being disposed in said frame, said first and second filter elements being successively superposed on said partition plate and pressed against said partition plate by said lids.

A yet further object of the present invention is to provide a liquid filtering device further comprising a mesh screen interposed between said first filter element and said partition plate.

A yet still further object of the present invention is to provide a liquid filtering device wherein said partition plate having a plurality of vertical rows of protrusions, said first filter element being pressed into gaps between said protrusions.

Still another object of the present invention is to provide a liquid filtering device wherein said partition plate has an upwardly convex portion directed toward said liquid inlet port.

Yet another object of the present invention is to provide a liquid filtering device wherein said lids have a plurality of elongate liquid guides on surfaces thereof facing said partition plate.

Yet still another object of the present invention is to provide a liquid filtering device for separating leukocytes from blood to produce concentrated red cells.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 2:
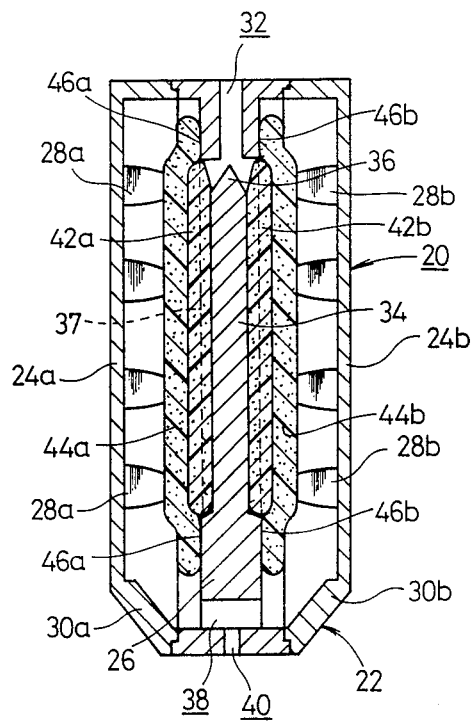
FIG. 2 is a vertical cross-sectional view of a liquid filtering device according to the present invention.

FIG. 2 shows a liquid filtering device, generally designated by the reference numeral 20, according to an embodiment of the present invention.

The liquid filtering device 20 has a housing 22 in the form of a flat plate assembly which basically comprises a first plate 24a, a second plate 24b, and a partition plate 26 sandwiched between the first and second plates 24a, 24b. The first and second plates 24a, 24b are symmetrically arranged and have a plurality of projections 28a, 28b extending from their inner wall surfaces toward the partition plate 26. The first and second plates 24a, 24b have respective tapered walls 30a, 30b on their lower ends.

The partition plate 26 is made of synthetic resin and has a liquid inlet port 32 defined in an upper end thereof and extending downwardly. The partition plate 26 has a central wall 34 of a narrow cross section having a tapered upper portion 36 directed toward the liquid inlet port 32. The central wall 34 has opposite wall surfaces recessed from outer side wall surfaces of the partition plate 26, thus defining recesses 37 in the partition plate 26. The partition plate 26 also has a transverse passage 38 defined in a lower portion thereof and a liquid or filtrate outlet port 40 defined in a lower end thereof. First and second filter elements 42a, 42b are partly disposed in the recesses 37 in sandwiching relation to the central wall 34.

The first filter elements 42a, 42b are coarser and have a smaller apparent density than second filter elements which will be described later on. The first filter elements 42a, 42b are preferably made of nonwoven fabric of polyester, nylon, or the like. The first and second filter elements 42a, 42b of such a material project laterally outwardly beyond the outer side wall surfaces of the partition plate 26.

Second filter elements 44a, 44b are mounted on the partition plate 26 in surrounding relation to the first filter elements 42a, 42b. The second filter elements 44a, 44b are bonded to flat surfaces 46a, 46b of the partition plate 26 by a strong adhesive so that no liquid will leak from between the partition plate 26 and the second filter elements 44a, 44b. If possible from a material standpoint, the flat surfaces 46a, 46b of the partition plate 26 and the second filter elements 44a, 44b may firmly united together by a high-frequency or ultrasonic fusing process. The second filter elements 44a, 44b are pressed against the first filter elements 42a, 42b by the projections 28a, 28b. As a result, the first filter elements 42a, 42b are pressed against the central wall 34 under a certain pressure.

The liquid filtering device 20 is basically constructed as described above. Operation and advantages of the liquid filtering device 20 will be described below.

Figure 3:
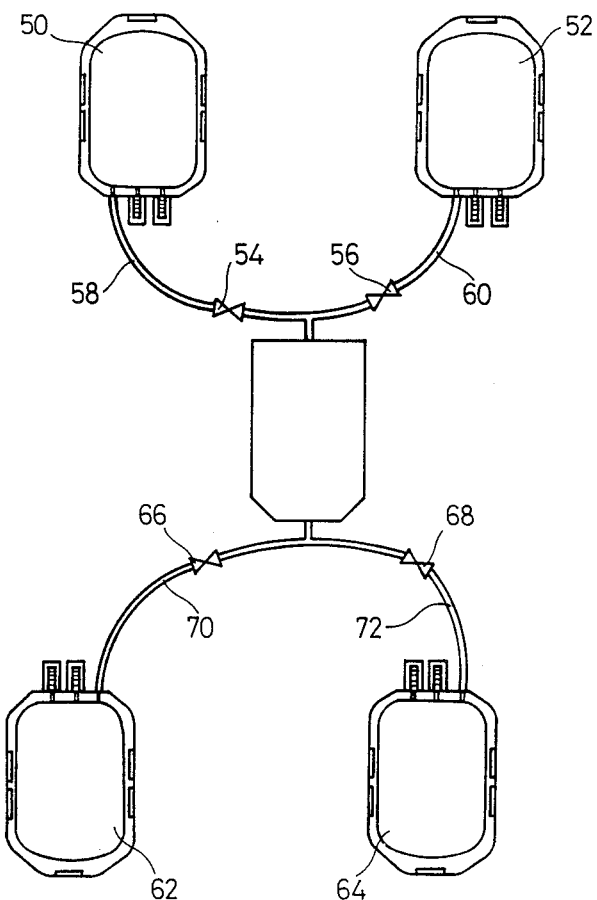
FIG. 3 is a schematic view showing a blood separation circuit incorporating the liquid filtering device of the invention.

The liquid filtering device 20 may be incorporated in a liquid processing circuit such as a blood separation circuit as shown in FIG. 3 for removing leukocytes from blood, for example. The blood separation circuit includes a blood bag 50 for containing blood from which leukocytes are to be removed and a physiological saline bag 52 for containing a physiological saline, the bags 50, 52 being positioned above the liquid filtering device 20. The bags 50, 52 have fluid outlets connected to the liquid inlet port 32 of the liquid filtering device 20 through a pair of liquid conduits 58, 60 having clamps 54, 56 respectively thereon.

The blood separation circuit also includes a physiological saline bag 62 for collecting the physiological saline and a blood bag 64 for collecting the blood from which leukocytes have been removed, the bags 62, 64 being positioned below the liquid filtering device 20. The bags 62, 64 have fluid inlets connected to the liquid outlet port 40 of the liquid filtering device 20 through a pair of liquid conduits 70, 72 having clamps 66, 68 respectively thereon.

A process of separating leukocytes from blood is carried out as follows: The clamps 56, 66 are opened and the clamps 54, 68 are closed to allow the physiological saline to flow from the physiological saline bag 52 into the liquid filtering device 20 to prime the same. The physiological saline which flows down through the liquid filtering device 20 is collected into the physiological saline collecting bag 62.

After the liquid filtering device 20 has been primed, the clamps 54, 68 are closed and the clamps 56, 66 are opened to allow the blood to flow from the blood bag 50 into the liquid filtering device 20. More specifically, the blood which has been introduced into the liquid inlet port 32 of the liquid filtering device 20 is divided by the tapered portion 36 of the central wall 34 into two flows which are directed toward the first filter elements 42a, 42b. The blood which has passed through the relatively coarse first filter elements 42a, 42b reach the second filter elements 44a, 44b by which leukocytes are trapped. Only red cells pass through the second filter elements 44a, 44b and then flow through the passage 38 into the liquid outlet port 40. The red cells are then discharged from the liquid outlet port 40 and collected via the liquid conduit 52 into the blood bag 64. During this time, since the second filter elements 44a, 44b are securely fixed to the flat surfaces 46a, 46b of the central wall 34, the red cells are prevented from leaking out from between the second filter elements 44a, 44b and the flat surfaces 46a, 46b.

After all the blood has been introduced into the blood bag 64, the clamp 56 is opened again in order to collect any blood remaining in the liquid filtering device 20. The physiological saline is supplied again into the liquid filtering device 20 via the clamp 56 to force he remaining blood out of the liquid filtering device 20 into the blood bag 64.

After the remaining blood has been collected, the clamp 68 is closed, and the clamp 66 is opened to collect the physiological saline, which was used to collect the remaining blood, into the physiological saline 62. The process of separating leukocytes from the blood is now finished.

A comparative experiment was conducted on various inventive examples of the liquid filtering device 20 of the present invention and various comparative examples of the conventional liquid filtering device 2 to determine leukocyte removal ratios and blood processing times. The results of the comparative experiment are given in Table below.

TABLE

| Inventive example | Leukocyte removal ratio (%) | Blood processing time (minutes) |
| --- | --- | --- |
| 1 | 95.5 | 5.7 |
| 2 | 96.8 | 7.7 |
| 3 | 95.9 | 6.9 |
| 4 | 97.7 | 5.4 |
| 5 | 95.8 | 6.3 |
| Average | 96.4 | 6.4 |
| Comparative example | Leukocyte removal ratio (%) | Blood processing time (minutes) |
| 1 | 75.6 | 4.5 |
| 2 | 69.8 | 3.4 |
| 3 | 71.5 | 7.8 |
| 4 | 67.6 | 5.7 |
| 5 | 79.3 | 9.2 |
| Average | 72.8 | 6.1 |

In the inventive examples 1 through 5, the first filter elements 42a, 42b were made of polyester felt having a smaller apparent density than the second filter elements 44a, 44b. The second filter elements 44a, 44b were made of a porous synthetic resin material such as polyvinyl formal "Bell Eater" (transliterated - registered trademark in Japan, manufactured by Kanebo, Ltd.). The first filter elements 42a, 42b had a smaller filtration area than the second filter elements 44a, 44b, and the second filter elements 44a, 44b were ultrasonically fused to the partition plate 26 to sandwich the first filter elements 42a, 42b.

Figure 1:
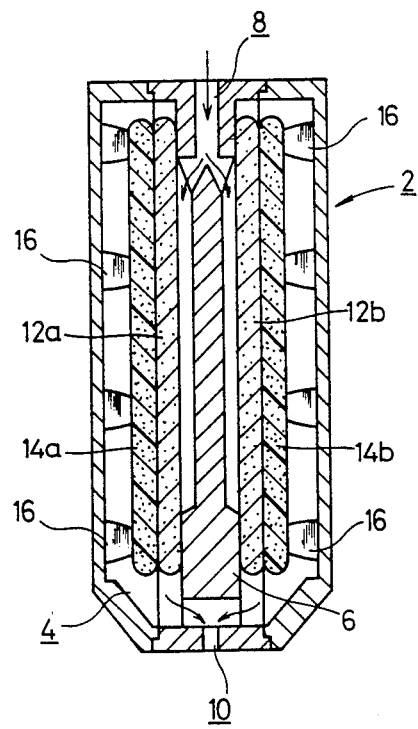
FIG. 1 is a vertical cross-sectional view of a conventional liquid filtering device.

In the comparative examples 1 through 5, the first and second filter elements were made of the same materials as those of the inventive examples 1 through 5. The first and second filter elements had the same filtration areas, and were pressed against the partition plate 6 as shown in FIG. 1.

400 ml of blood was filtered under a maximum pressure of 500 mm aq by the liquid filtering devices according to the inventive examples 1 through 5 and the comparative examples 1 through 5, and leukocyte removal ratios and blood processing times were measured.

As can be seen from Table above, the leukocyte removal ratios of the tested liquid filtering devices according to the present invention ranged from 95.6 % to 97.7 %, and their average was 96.4 %. The leukocyte removal ratios of the conventional liquid filtering devices were scattered in a wider range and lower than those of the liquid filtering devices of the invention. The blood processing times of the liquid filtering devices of the invention were in the range of from 5.4 minutes to 7.7 minutes, and their average was 6.4 minutes. The blood processing times of the conventional liquid filtering devices ranged from 3.4 minutes to 9.2 minutes, and their average was 6.1 minutes. The blood processing times of the conventional liquid filtering devices were not largely different from those of the inventive liquid filtering devices, but had widely different leukocyte removal ratios and could not perform stable filtering operation.

Figure 4:
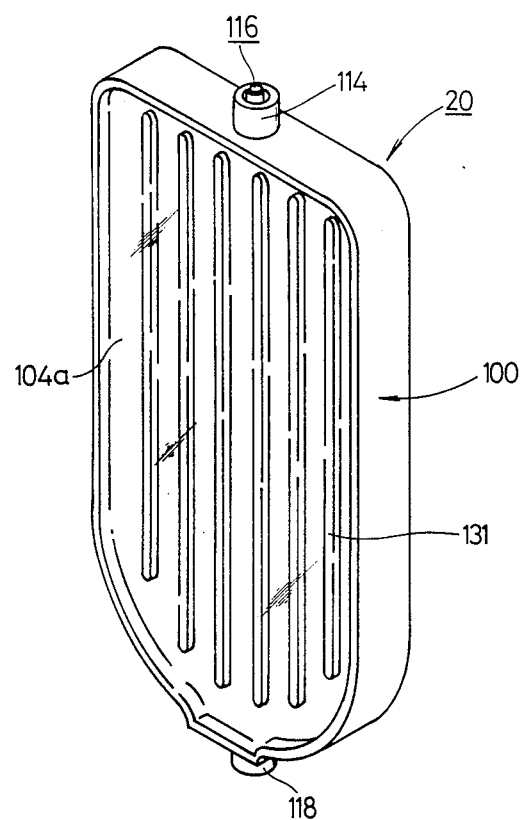
FIG. 4 is a perspective view of a liquid filtering device according to another embodiment of the present invention.
Figure 5:
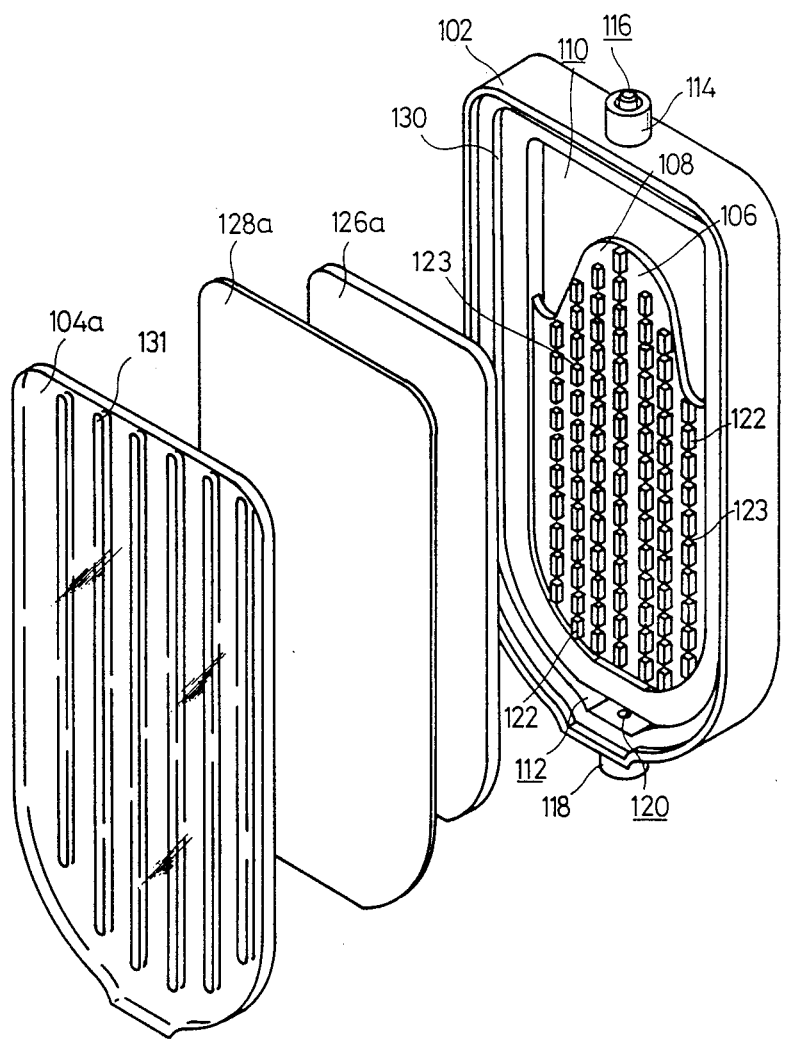
FIG. 5 is an exploded perspective view of the liquid filtering device shown in FIG. 4.
Figure 6:
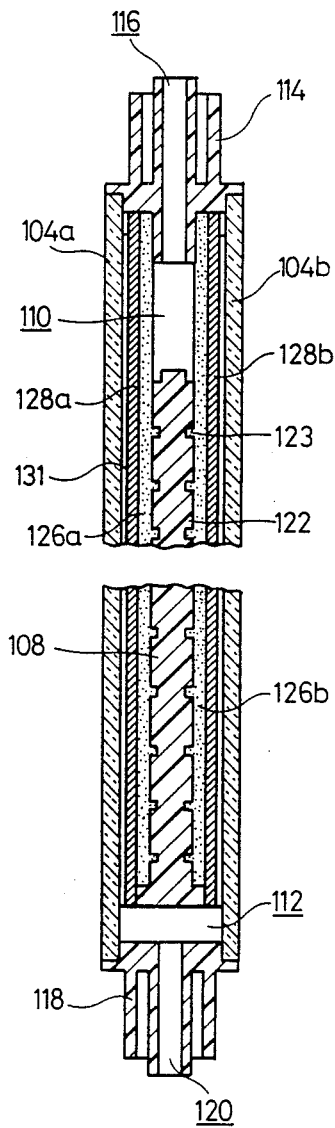
FIG. 6 is a fragmentary vertical cross-sectional view of the liquid filtering device illustrated in FIGS. 4 and 5.

FIGS. 4 through 6 illustrate a liquid filtering device according to another embodiment of the present invention. As shown in FIGS. 4 through 6, the liquid filtering device 20 includes a housing 100 made of synthetic resin and comprising a wide frame 102 having a converging lower end, and a pair of lids 104a, 104b fitted in the frame 102 in spaced-apart relation to each other. The lids 104a, 104b are secured to the frame 102 in a liquid-tight manner by an ultrasonic or high-frequency fusing process or an adhesive. The frame 102 has an integral partition plate 106 which divides the interior of the housing 100 into two chambers which are also defined by the frame 102 and the lids 104a, 104b.

As shown in FIG. 5, the partition plate 106 has a central portion 108 including an upwardly convex upper portion leaving a space 110 in an upper portion of the frame 102. The partition plate 106 also has a downwardly converging lower end in a lower portion of the frame 102, leaving a space 112 between the lower end of the partition plate 106 and the frame 102. The frame 102 has a cylindrical projection 114 on its top which defines a liquid inlet port 116 axially therethrough. The frame 106 also has a cylindrical projection 118 on its bottom which defines a liquid outlet port 120 axially therethrough. The space 110 communicates with the liquid inlet port 116, whereas the space 112 communicates with the liquid outlet port 120.

The partition plate 106 has a plurality of vertical rows of protrusions 122 on each of its side surfaces, defining passages 123 between the protrusions 122 in a horizontal direction normal to the rows of the protrusions 122.

First filter elements 126a, 126b are disposed one on each side of the partition plate 106 in covering relation to the partition plate 106 and the space 110. Second filter elements 128a, 128b are placed over the respective first filter elements 126a, 126b. The second filter elements 128a, 128b have ends held against an engaging ridge 130 projecting from a peripheral edge of the frame 102. The lids 104a, 104b are disposed in the frame 102 in superposed relation to the second filter elements 128a, 128b, respectively, thus closing the chambers in the frame 102 completely in a liquidtight manner. Each of the lids 104a, 104b has a plurality of vertical elongate guides 131 on an inner surface thereof.

The liquid filtering device 20 thus constructed is preferably employed in the blood separation system illustrated in FIG. 3 for separating leukocytes from blood. More specifically, when blood is introduced into the liquid inlet port 116, the blood first enters the space and then flows therefrom onto the upwardly convex central portion 108 of the partition plate 106 by which the blood is divided into horizontally opposite areas in the frame 102. The blood as it flows downwardly is then directed vertically by the protrusions 122 and horizontally by the passages 123.

As shown in FIG. 6, the first filter elements 126a, 126b are sufficiently pressed into the passages 123 and disposed in vertical gaps between the rows of the passages 123. Therefore, the blood necessarily penetrates the first filters 126a, 126b, and then enters the second filter elements 128a, 128b. Therefore, leukocyters are removed from the blood by the first filter elements 126a, 126b and the second filter elements 128a, 128b. Concentrated red cells which have passed through the second filter elements 128a, 128b flows along the guides 131 on the lids 104a, 104b into the space 112, from which the concentrated red cells are discharged via the filtrate outlet port 120 into the blood bag 64 (FIG. 3).

A liquid filtering device according to still another embodiment of the present invention will be described with reference to FIGS. 7 and 8. Those components of the liquid filtering device shown in FIGS. 7 and 8 which are identical to those of FIGS. 4 through 6 are denoted by identical reference numerals, and will not be described in detail.

Figure 7:
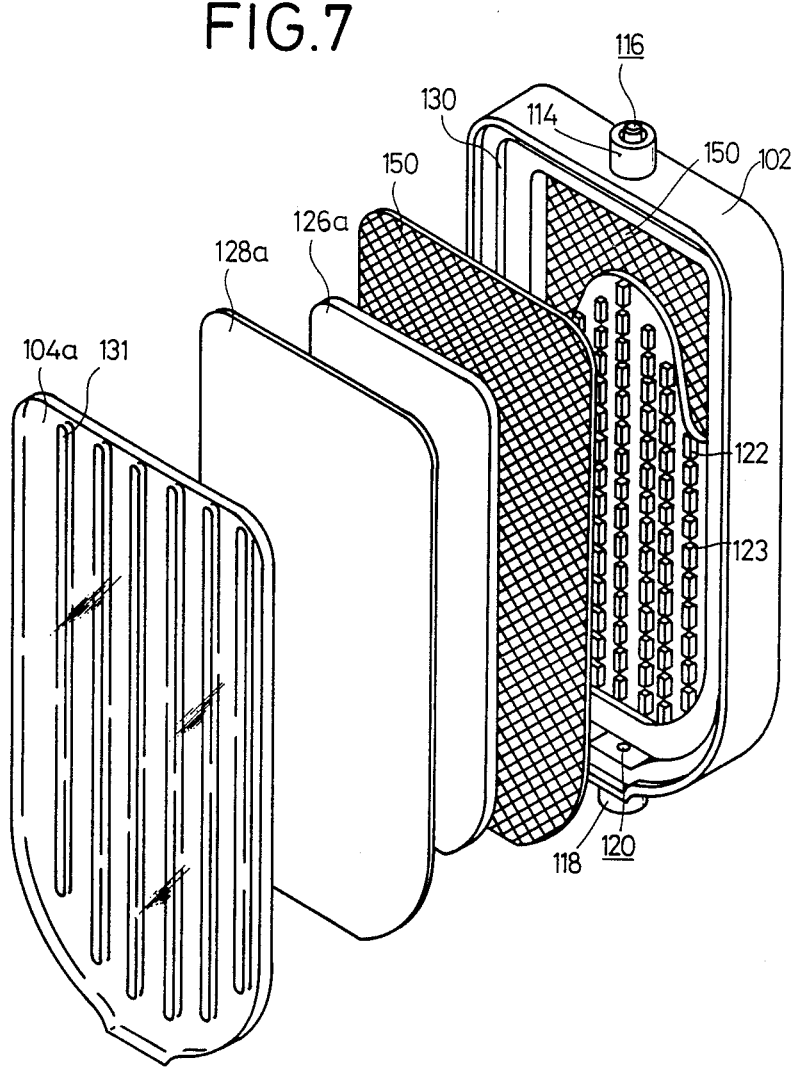
FIG. 7 is an exploded perspective view of a liquid filtering device in accordance with still another embodiment of the present invention.
Figure 8:
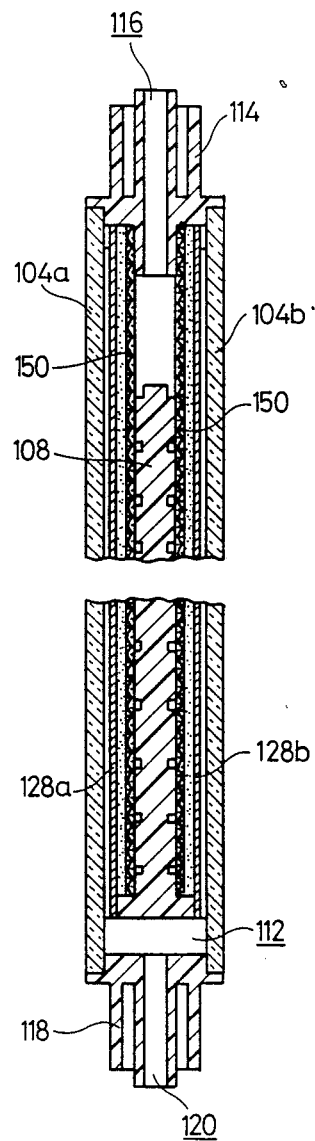
FIG. 8 is a fragmentary vertical cross-sectional view of the liquid filtering device shown in FIG. 7.

As shown in FIGS. 7 and 8, a pair of mesh screens 150 is disposed in the frame 102 at positions closest to the partition plate 106. More specifically, the mesh screens 150 are positioned one on each side of the partition plate 106, and the first filter elements 126a, 126b, the second filter elements 128a, 128b, and the lids 104a, 104b are successively disposed over the mesh screens 150. The mesh screens 150 allow the second filter elements 128a, 128b to be bonded easily to the frame 102 by a high-frequency or ultrasonic fusing process. Blood to be filtered can easily enter the first filter elements 126a, 126b and the second filter elements 128a, 128b since the blood flows downwardly in different directions through the mesh openings of the mesh screens 150.

With the present invention, as described above, since the second filter elements are bonded to the partition plate, blood introduced into the liquid filtering device from the liquid inlet port is always guided to enter the second filter elements without any short pass toward the filtrate outlet port of the device. As a consequence, leukocytes are effectively removed from the blood to produce desired concentrated red cells. Stated otherwise, inasmuch as the blood flows successively through the first filter elements and the second filter elements, unwanted components are effectively filtered out from the blood by the filter elements, and the filter elements are less subjected to clogging. Because the second filter elements are fused or bonded to the partition plate, the first filter elements are prevented from being peeled off by the second filter elements. The liquid filtering device provides stable liquid filtering performance as the filter elements are less liable to clog.

Although certain preferred embodiments have been shown and described, it should be understood that many changes and modifications may be made therein without departing from the scope of the appended claims.

What is claimed is:

1. A liquid filtering device comprising:
    a housing having a liquid inlet port and a liquid outlet port;
    a partition plate fixedly disposed in said housing;
    a first filter element disposed in said housing; and
    a second filter element disposed in said housing in a position downstream of said first filter element with respect to a direction in which a liquid to be filtered flows from said liquid inlet port to said liquid outlet port, said second filter element being made of a material having a larger filtration resistance than said first filter element, said second filter element having an outer peripheral edge fixed directly to said partition plate in a liquidtight manner in surrounding relation to said first filter element.

2. A liquid filtering device according to claim 1, wherein said housing comprises a frame and a pair of lids fitted in opposite sides of said frame and closing the frame in a liquidtight manner, said partition plate being disposed in said frame, said first and second filter elements being successively superposed on said partition plate and pressed against said partition plate by said lids.

3. A liquid filtering device according to claim 2, further comprising a mesh screen interposed between said first filter element and said partition plate.

4. A liquid filtering device according to claim 1, wherein said partition plate has a plurality of vertical rows of protrusions, said first filter element being pressed into gaps between said protrusions.

5. A liquid filtering device according to claim 1, wherein said partition plate has an upwardly convex portion directed toward said liquid inlet port.

6. A liquid filtering device according to claim 1, wherein said lids have a plurality of elongate liquid guides on surfaces thereof facing said partition plate.

7. A liquid filtering device according to claim 1, for separating leukocytes from blood to produce concentrated red cells.

8. A liquid filtering device according to claim 1, wherein said outer peripheral edge of the second filter element which is liquidtightly fixed to the partition plate extends beyond an edge of said first filter element.

* * * * *